United States Patent [19]
Twyford, Jr.

[11] Patent Number: 5,109,867
[45] Date of Patent: May 5, 1992

[54] EXTENDABLE GUIDEWIRE ASSEMBLY
[75] Inventor: Robert H. Twyford, Jr., Palo Alto, Calif.
[73] Assignee: Target Therapeutics, Santa Clara, Calif.
[21] Appl. No.: 688,915
[22] Filed: Apr. 19, 1991
[51] Int. Cl.⁵ .............................. A61B 5/00
[52] U.S. Cl. ................. 128/772; 128/657; 403/223
[58] Field of Search ............. 128/657, 772; 604/164, 604/283; 403/223

[56] References Cited

U.S. PATENT DOCUMENTS

| | | | |
|---|---|---|---|
| 4,827,941 | 5/1989 | Taylor et al. | 128/657 |
| 4,875,489 | 10/1989 | Messner et al. | 128/772 |
| 4,884,579 | 12/1989 | Engelson | 128/772 |
| 4,917,103 | 4/1990 | Gambale et al. | 128/772 |
| 4,922,923 | 5/1990 | Gambale et al. | 128/772 |
| 4,966,163 | 10/1990 | Kraus et al. | 128/772 |

*Primary Examiner*—Max Hindenburg
*Attorney, Agent, or Firm*—Morrison & Foerster

[57] ABSTRACT

An extendable guidewire assembly comprising: a guidewire whose proximal end carries a first axial interlocking member; and extension wire whose distal end carries (i) a second axial interlocking member that is adapted to overlap and axially interlock with the first member and (ii) a retractable sleeve that is retracted to permit the interlocking members to be interlocked and extended to enclose the interlocked members to maintain their interlocked relationship.

9 Claims, 3 Drawing Sheets

EXTENDABLE GUIDEWIRE ASSEMBLY

TECHNICAL FIELD

This invention is in the general field of surgical instruments and relates specifically to guidewires that are used in cardiovascular and endovascular procedures to facilitate the placement of catheters within the vasculature of patients.

BACKGROUND

The general procedure for placing catheters within vessels is to track a guidewire through the vessel to the desired position and advance the catheter over the guidewire. Guidewires are required because the catheters themselves do not have sufficient column strength or torqueability to be able to be tracked or steered through the vessel. See, for instance, U.S. Pat. No. 4,884,579.

In some procedures such as angioplasty using dilatation balloon catheters, it is necessary to exchange catheters to increase balloon size. It may also be necessary in some instances to replace catheters due to material fatigue. Two guidewire techniques have been employed in such instances. In one, the initial guidewire is removed and replaced with an exchange wire that is somewhat greater than double the length of the catheter. In order to avoid the need for a separate exchange wire a second technique that involves attaching an extension wire to the initial guidewire was developed.

U.S. Pats. Nos. 4,917,103 and 4,922,923 describe an extendable guidewire assembly that employs a sleeve that is connected to the proximal end of the guidewire and into which the distal end of the extension wire is inserted. The sleeve and extension are then crimped to form a permanent joint or union between the two wires.

U.S. Pat. No. 4,875,489 describes another type of extendable guidewire assembly in which one of the wires has a tapered tip and the other has an expandable sleeve into which the tip is received. A second concentric sleeve encloses the expandable sleeve to ensure a friction fit between the tapered tip and expandable sleeve.

U.S. Pat. No. 4,966,163 describes yet another kind of extendable guidewire assembly. In this assembly one of the wires carries an internally threaded sleeve and the other wire carries a threaded head. The two wires are coupled together by threading the head into the sleeve.

Applicant is also aware of an extendable guidewire assembly design in which one of the wires carries an open-ended sleeve and the other wire has a tapered tip encircled by a helical coil. The wires are coupled by inserting the tip into the sleeve and twisting it. The twisting causes the coil to expand and form a friction fit with the interior of the sleeve. The wires are uncoupled by twisting the tapered tip wire in the reverse direction.

A primary object of the present invention is to provide an extendable guidewire assembly that may be connected and disconnected and is relatively simple to manufacture.

DISCLOSURE OF THE INVENTION

The invention is an extendable guidewire assembly for use within a patient's vasculature comprising in combination:

(a) a guidewire having a distal end that is adapted to be fed into said vasculature and a proximal end that has a first longitudinal (axial) interlocking member;

(b) an extension wire having a proximal end and a distal end that has a second longitudinal interlocking member that is adapted to longitudinally overlap and interlock with the first interlocking member; and (c) a retractable sleeve carried concentrically about one of either the proximal end of the guidewire or the distal end of the extension wire, the sleeve being longitudinally movable from a retracted position in which it does not enclose an interlocking member to an extended position in which it encloses the overlapped, interlocked members to prevent said members from substantial radial movement relative to each other.

BRIEF DESCRIPTION OF THE DRAWINGS

In the drawings.

Like parts in the assemblies shown in the drawings bear the same reference numerals.

MODES FOR CARRYING OUT THE INVENTION

Figure 1:
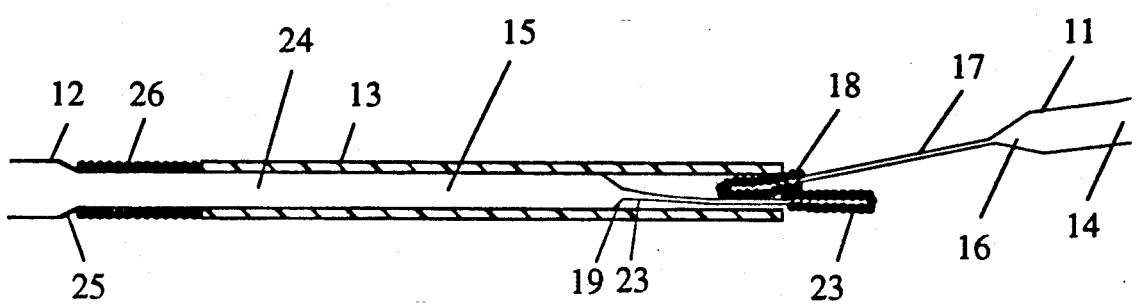
FIG. 1 is a fragmentary elevational view, partially in section, of a first embodiment of the extendable guidewire assembly with the assembly partly disconnected.
Figure 2:
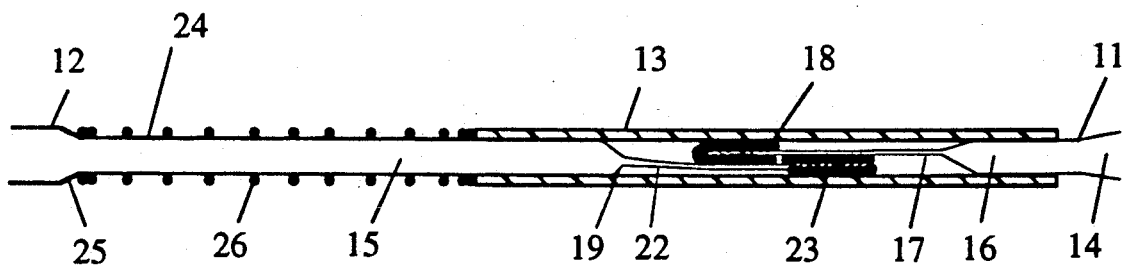
FIG. 2 is a fragmentary elevational view of the embodiment of FIG. 1 with the assembly connected.

FIGS. 1 and 2 illustrate the preferred embodiment of the extendable guidewire assembly of the invention. The three principal components of the assembly are: a guidewire 11, an extension wire 12, and a sleeve 13. In these figures only the proximal end 14 of the guidewire and the distal end 15 of the extension wire are shown. The remainders of the components are not shown and are of conventional structure.

While this invention may be produced with guidewires of any length and diameter, it will typically be employed with stainless steel or nickel-titanium alloy guidewires and extensions that are $\leq 0.46$ mm in diameter, more normally 0.30 to 0.41 mm in diameter. In most instances the length of the guidewire will be in the range of 100–200 cm and the extension will be on the order of 125 to 225 cm in length.

The proximal end 14 of guidewire 11 has a tapered section 16 and an elongated small diameter tip 17. Tip 17 is deformable and, in the case of a 0.36 mm diameter wire, will typically have a diameter in the range of 0.08 to 0.15 mm and a length of 0.2 to 0.7 cm. A tightly wound coil 18 is affixed to the end of the tip such as by soldering. The outer diameter of the coil is greater than ½ the inner diameter of the sleeve and will normally be 0.10 to 0.20 mm. The length of the coil will normally be 0.2 to 0.7 cm.

The distal end 15 of extension wire 12 similarly tapers at 19 to an elongated tip 22. A tightly wound coil 23 is similarly affixed to the end of tip 22. The dimensions of tip 22 and coil 23 are in the same ranges as the dimensions of tip 17 and coil 18. Proximal to taper 19 is a reduced diameter segment 24 of extension wire 15. In the case of a 0.36 mm diameter extension wire, the diameter of segment 24 will normally be 0.20 to 0.25 mm. Segment 24 extends between 19 and a second taper 25 and will normally be about 2.0 cm to 10.0 cm in length. Sleeve 13 is carried concentrically about segment 24 as is a coil spring 26. The proximal end of coil spring 26 is connected to the inner end of taper 25. Its distal end is affixed to the proximal end of sleeve 13. The spring serves to bias the sleeve distally. The outer diameters of coil 26 and sleeve 13 are preferably less than or equal to that of the diameter of the main body of the extension wire (proximal to 25). Also, the diameter of the proximal end 14 of guidewire 11 is such that it may be received within the lumen of sleeve 13.

Sleeve 13 is retractable, that is, it is slidable on segment 24 from a retracted position (FIG. 1) in which spring 26 is compressed and the entire portion of tip 22 that is wrapped in coil is exposed, to an extended position (FIG. 2) in which the tip 22 is entirely enclosed. For use with guidewires and extensions of the above-described dimensions, the sleeve will normally have an outer diameter of about 0.36-0.46 mm, an inner diameter of 0.2 to 0.30 mm and a length of 1 to 8 cm.

In the embodiment depicted in FIGS. 1 and 2 the guidewire and extension wire connect as follows. The sleeve 13 is retracted to the position shown in FIG. 1 by exerting axial force on the sleeve in the proximal direction. The coil-wrapped tip 17 of the guidewire is then inserted into the open (distal) end of the sleeve so that it rests between the unwrapped portion of tip 22 and the inner wall of the sleeve. The axial force on the sleeve is then removed and the sleeve is slid distally by the force exerted by spring 26 so that it encloses both tips 17 and 22 and portions of segment 24 of the extension and end 14 of the guidewire. The sleeve is dimensioned such that its inside diameter is less than the combined outside diameters of the coil-wrapped portions of tips 17, 22. Accordingly, as shown in FIG. 2, the tips 22 axially or longitudinally overlap each other with the ends of the coil wrappings abutting in a longitudinally interlocking relationship. In this regard, the sleeve prevents substantial radial movement of the interlocked tips thus ensuring that the tips remain axially interlocked. The guidewire and extension may be disconnected by retracting the sleeve to a position such that tip 17 may be moved radially and withdrawn from its overlapping position with tip 22.

Figure 3:
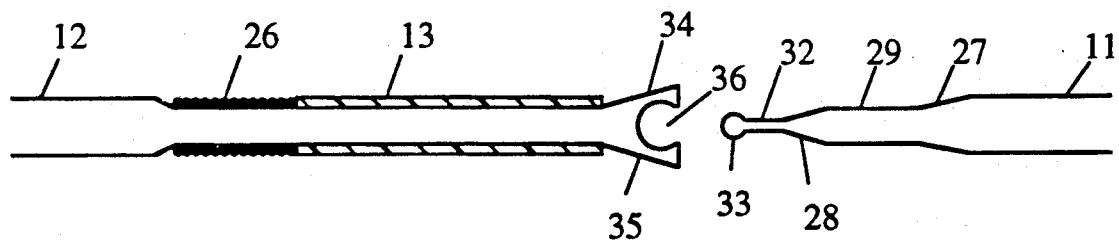
FIG. 3 is a fragmentary elevational view, partially in section, of a second embodiment of the extendable guidewire assembly with the assembly disconnected.
Figure 4:
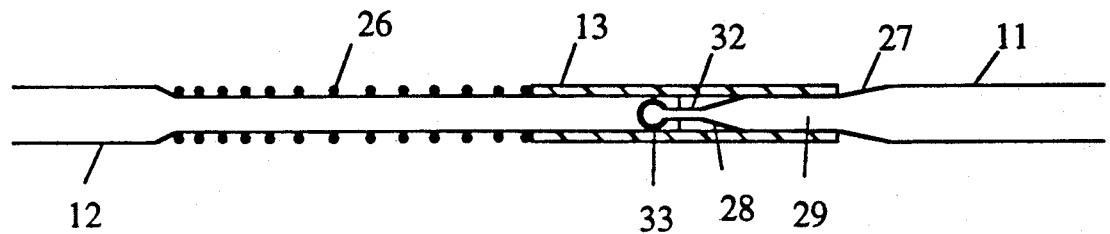
FIG. 4 is a fragmentary elevational view of the embodiment of FIG. 2 with the assembly connected.

FIGS. 3 and 4 depict another embodiment of the invention assembly. In this embodiment, the main bodies of the guidewire and extension wire and the retractable sleeve are structured as in the embodiment of FIGS. 1 and 2. Only the structures of the interlocking tips of the guidewire and extension wire differ from those of the embodiment of FIG. 1. The tip of the guidewire 11 has a pair of tapers at 27 and 28 that define a reduced diameter segment 29. The diameter of segment 29 is less than the inner diameter of the sleeve. Proximally of taper 28 is a second segment 32 of still smaller diameter that terminates in a ball 33. Correspondingly, the distal end of extension wire 12 has a pair of radially expandable resilient jaw members 34, 35 that define a generally spherical socket 36. When the sleeve 13 is retracted (FIG. 3), the jaws are open. When the sleeve is in its extended position (FIG. 4), it exerts radial force on the jaws to close them. Thus, the following procedure is employed to connect the guidewire and extension wire of this embodiment. The sleeve is retracted to a position proximal of jaws 34 and 35 allowing the jaws to open. The ball 33 on the proximal end of the guidewire is then inserted into socket 36. The sleeve is then released to permit it to slip over the jaws and close them about ball 33.

Figure 5:
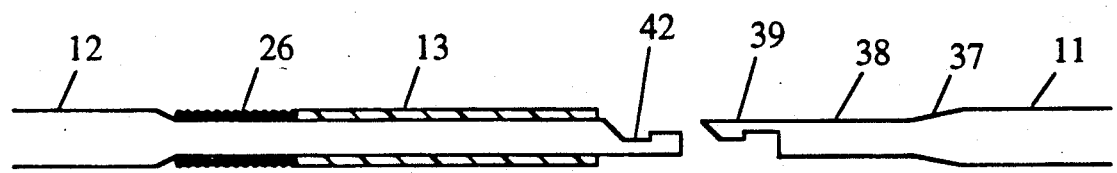
FIG. 5 is a fragmentary elevational view, partially in section, of a third embodiment of the extendable guidewire assembly with the assembly disconnected.
Figure 6:
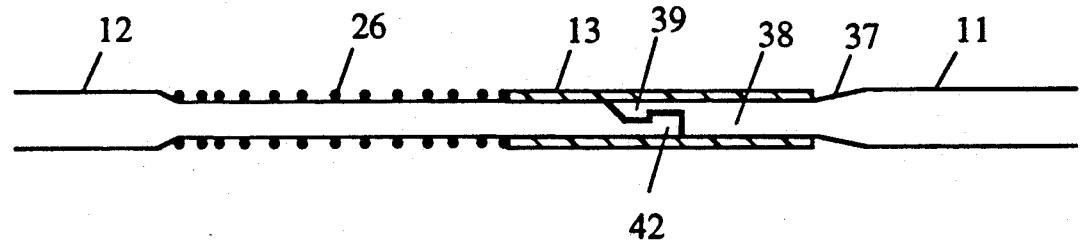
FIG. 6 is a fragmentary elevational view of the embodiment of FIG. 5 with the assembly connected.

FIGS. 5 and 6 show yet another embodiment of the invention. Again only the structures of the tips of the guidewire and extension wire differ in structure from the previously described embodiments. In this embodiment the proximal end of the guidewire has a taper at 37 and a reduced diameter tip 38. The end of the tip is formed into a locking tang 39. Correspondingly, the distal end of the extension wire is formed into a second locking tang 42 that is configured to interlock with tang 39. The guidewire and extension are connected by retracting (FIG. 5) sleeve 13 to expose tang 42, positioning tang 39 to interlock with tang 42, and releasing the sleeve so that it encloses the interlocked tangs (FIG. 6).

Figure 7:
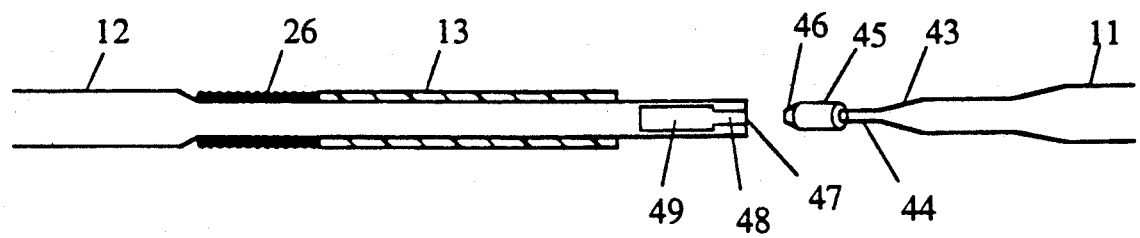
FIG. 7 is a fragmentary perspective view of a fourth embodiment of the extendable guidewire assembly with the assembly disconnected.
Figure 8:
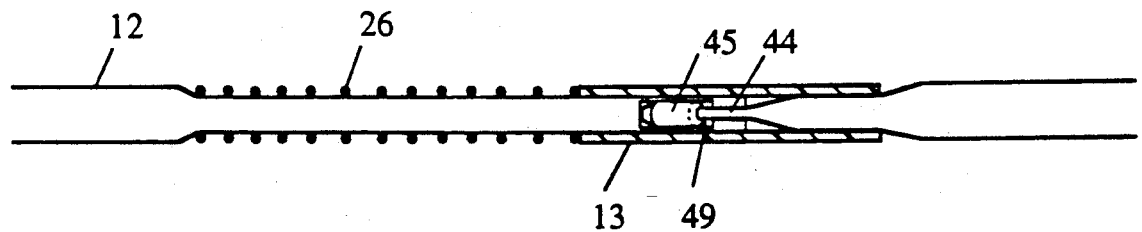
FIG. 8 is a fragmentary perspective view of the embodiment of FIG. 7 with the assembly connected.

FIGS. 7 and 8 illustrate a fourth embodiment of the invention. Again only the structures of the tips of the guidewire and extension wire differ in structure from the previously described embodiments. In this embodiment the proximal end of the guidewire has a taper at 43, a reduced diameter segment 44, and a generally cylindrical head 45 with a tapered end 46. The distal end of the extension wire has a cylindrical bore 47 of slightly smaller diameter than the diameter of head 45. The length of the bore is at least the combined length of the head 45 and reduced diameter segment 44. A first axial slot 48 in the extension wire extends radially from the surface of the wire through to the bore 47 and axially from the end of the wire. This slot opens into a second slot 49 whose radial dimension is equal to or greater than the diameter of head 45. The guidewire and extension wire of this embodiment are connected as follows. The sleeve is retracted (as seen in FIG. 7). The tapered end of the head 45 is then inserted into the opening of bore 47 and axial force is applied. The slot 48 permits the bore 47 to expand slightly to permit the head 45 to be forced into the bore until the head is seated in registry with the slot 49 (as seen in FIG. 2). Once the head reaches that position the radial expansion exerted on the distal segment of bore 47 by the head is relieved and the distal segment snaps shut behind the head, thus axially locking the head in place. The sleeve is then moved to its extended position (FIG. 2) to enclose the ends of the wires. The wires may be disconnected by retracting the sleeve and lifting the guidewire tip out of the bore via the slots 48, 49.

While the above-described embodiments all show the sleeve being carried on the extension, it will be appreciated that the respective tip structures may be reversed (i.e., the sleeve, etc., carried on the guidewire). Similarly, other modifications of these embodiments that are obvious to those of skill in the mechanical and guidewire/catheter arts are intended to be within the scope of the following claims.

I claim:

1. An extendable guidewire assembly for use within a patient's vasculature comprising in combination:

(a) a guidewire having a distal end that is adapted to be fed into said vasculature and a proximal end that has a first longitudinal interlocking member;

(b) an extension wire having a proximal end and a distal end that has a second longitudinal interlocking member that is adapted to longitudinally overlap and interlock with the first interlocking member; and (c) a retractable sleeve carried concentrically about one of either the proximal end of the guidewire or the distal end of the extension wire, the sleeve being longitudinally movable from a retracted position in which it does not enclose an interlocking member to an extended position in which it encloses the overlapped, interlocked members to prevent said members from substantial radial movement relative to each other.

2. The extendable guidewire assembly of claim 1 wherein the retractable sleeve is carried about the distal end of the extension wire.

3. The extendable guidewire assembly of claim 1 wherein the assembly includes biasing means for biasing the sleeve to said extended position.

4. The extendable guidewire assembly of claim 3 wherein the biasing means is a coil spring.

5. The extendable guidewire assembly of claim 1 wherein the first interlocking member comprises a longitudinal tip of less diameter than the diameter of the proximal end of the guidewire, one end of which is integral with the guidewire and the other end of which carries a first radial protuberance, and the second interlocking member comprises a longitudinal tip of less diameter than the diameter of the distal end of the guidewire extension, one end of which is integral with the extension wire and the other end of which has a second radial protuberance, the inner diameter of the sleeve being less than the combined diameters of the first and second radial protuberances.

6. The extendable guidewire assembly of claim 5 wherein the first radial protuberance comprises a first coil wrapped about said other end of the longitudinal tip of the guidewire and said second radial protuberance comprises a second coil wrapped about said other end of the longitudinal tip of the extension wire.

7. The extendable guidewire assembly of claim 1 wherein the first interlocking member comprises a ball and the second interlocking member comprises a pair of radially extendable resilient jaws that define a socket adapted to receive said ball.

8. The extendable guidewire assembly of claim 1 wherein the first interlocking member comprises a first tang and the second interlocking member comprises a second tang adapted to interlock with the first tang.

9. The extendable guidewire assembly of claim 1 wherein the first interlocking member comprises a cylindrical head and the second interlocking member comprises a cylindrical bore in the distal end of the guidewire that is adapted to receive the cylindrical head.

* * * * *